United States Patent
Kawamura et al.

(10) Patent No.: US 8,962,012 B2
(45) Date of Patent: *Feb. 24, 2015

(54) NONAQUEOUS PRESSURE-SENSITIVE ADHESIVE FOR MEDICINAL TAPE PREPARATION FOR PERCUTANEOUS ABSORPTION, MEDICINAL TAPE PREPARATION FOR PERCUTANEOUS ABSORPTION, AND PROCESS FOR PRODUCING THE SAME

(71) Applicant: Nipro Patch Co., Ltd., Kasukabe-shi, Saitama (JP)

(72) Inventors: Naohisa Kawamura, Kasukabe (JP); Hidenori Sawada, Kasukabe (JP); Takayuki Kobayashi, Saitama (JP)

(73) Assignee: Nipro Patch Co., Ltd., Saitama (JP)

( * ) Notice: Subject to any disclaimer, the term of this patent is extended or adjusted under 35 U.S.C. 154(b) by 25 days.

This patent is subject to a terminal disclaimer.

(21) Appl. No.: 13/750,361

(22) Filed: Jan. 25, 2013

(65) Prior Publication Data

US 2013/0138056 A1 May 30, 2013

Related U.S. Application Data

(63) Continuation of application No. 12/460,146, filed on Jul. 14, 2009, now abandoned, which is a continuation of application No. 10/561,751, filed as application No. PCT/JP2004/008544 on Jun. 17, 2004, now abandoned.

(30) Foreign Application Priority Data

Jun. 24, 2003 (JP) ................... 2003-179162

(51) Int. Cl.
- *A61F 13/02* (2006.01)
- *A61L 24/04* (2006.01)
- *A61K 9/70* (2006.01)
- *A61K 47/32* (2006.01)
- *A61F 13/00* (2006.01)

(52) U.S. Cl.
CPC .............. *A61L 24/046* (2013.01); *A61K 9/7061* (2013.01); *A61K 47/32* (2013.01); *A61F 2013/00663* (2013.01)
USPC ........................................................ 424/448

(58) Field of Classification Search
None
See application file for complete search history.

(56) References Cited

U.S. PATENT DOCUMENTS

| 4,751,087 A | 6/1988 | Wick |
| H0000509 H | 8/1988 | Chao |
| 5,185,212 A | 2/1993 | Spada et al. |
| 5,435,879 A | 7/1995 | Knutson et al. |
| 5,798,426 A | 8/1998 | Anton et al. |
| 6,417,267 B1 | 7/2002 | Stockl et al. |

FOREIGN PATENT DOCUMENTS

| EP | 0701816 | 3/1996 | |
| EP | 1291025 | 3/2003 | |
| JP | 06-108033 | 4/1994 | |
| JP | 07-238203 | 9/1995 | |
| JP | 08-081369 | 3/1996 | |
| JP | 10-033657 | 2/1998 | |
| JP | 2002-535475 | 10/2002 | |
| JP | 2004-148221 | 5/2004 | |
| KR | 2003-19203 | 3/2003 | ............. A61K 47/30 |
| WO | 99/45896 | 9/1999 | |
| WO | 00/44846 | 8/2000 | |

OTHER PUBLICATIONS

Supplementary European Search Report dated Feb. 23, 2012, from the European Patent Office in corresponding European Application No. 04746059.7.

*Primary Examiner* — Nissa Westerberg
(74) *Attorney, Agent, or Firm* — Roylance, Abrams, Berdo & Goodman, L.L.P.

(57) ABSTRACT

The present invention is directed to a nonaqueous pressure-sensitive adhesive that may be used in medicinal tape preparations for percutaneous absorption. The adhesive may comprise a copolymer obtained by copolymerization of a (meth) acrylic monomer having an acetoacetyl group in the molecule and one or more monomers from among other (meth)acrylic monomers without acetoacetyl groups and copolymerizable vinyl monomers, in a nonaqueous solvent. Suitable (meth) acrylic monomers having an acetoacetyl group in the molecule are acetoacetoxyalkyl methacrylates, and especially 2-acetoacetoxyethyl methacrylate. The pressure-sensitive adhesive of the invention uses no polyamine derivatives, isocyanate compounds, polyvalent metal chelate compounds, etc., as crosslinking agents, and therefore toxicity is not a concern and skin is not irritated. A medicinal tape preparation for percutaneous absorption of the invention has superior adhesive strength and cohesive strength, and is highly safe with low skin irritation. It also has excellent drug release and percutaneous absorption properties.

10 Claims, No Drawings

NONAQUEOUS PRESSURE-SENSITIVE ADHESIVE FOR MEDICINAL TAPE PREPARATION FOR PERCUTANEOUS ABSORPTION, MEDICINAL TAPE PREPARATION FOR PERCUTANEOUS ABSORPTION, AND PROCESS FOR PRODUCING THE SAME

CROSS-REFERENCE TO RELATED APPLICATIONS

The present application is a continuation application of, and claims benefit of, U.S. patent application Ser. No. 12/460,146, filed on Jul. 14, 2009, which was a continuation application of, and claimed benefit of, U.S. patent application Ser. No. 10/561,751, filed on Dec. 21, 2005, which was the national stage of, and claimed benefit of, International Application PCT/JP2004/008544, filed on Jun. 17, 2004, which claims benefit of, and priority to, Japanese Patent Application No. 2003-179162, filed on Jun. 24, 2003, all of which are herein incorporated by reference.

TECHNICAL FIELD

The present invention relates to a nonaqueous pressure-sensitive adhesive for a medicinal tape preparation for percutaneous absorption, comprising a copolymer obtained by copolymerization of a (meth)acrylic monomer having an acetoacetyl group in the molecule and one or more monomers selected from among other (meth)acrylic monomers with no acetoacetyl group and copolymerizable vinyl monomers, in a nonaqueous solvent, as well as to a medicinal tape preparation for percutaneous absorption produced by coating a nonaqueous pressure-sensitive adhesive onto the top side of a support or release film, together with a drug and plasticizer, and heating to dryness to form a pressure-sensitive adhesive layer, and then further laminating a release film or support over the pressure-sensitive adhesive layer, and to a process for producing the same. The medicinal tape preparation for percutaneous absorption according to the invention is a highly stable tape preparation for percutaneous absorption which exhibits excellent drug release from the preparation and excellent drug skin permeability, with low skin irritation.

BACKGROUND ART

Paints, coatings and pressure-sensitive adhesives are known wherein copolymers obtained by copolymerization of acetoacetoxyalkyl methacrylates and other monomers are crosslinked with crosslinking agents such as polyamine compounds or isocyanate compounds. (See, for example, Patent document 1 and Patent document 2). However, no patent document or non-patent document can be found which describes the use of a nonaqueous pressure-sensitive adhesive comprising a copolymer obtained by copolymerization of a (meth)acrylic monomer having an acetoacetyl group, and one or more monomers selected from among other (meth)acrylic monomers and copolymerizable vinyl monomers, as the pressure-sensitive adhesive used in a medicinal tape preparation for percutaneous absorption.

Tape preparations for percutaneous absorption have been known which comprise a drug and plasticizer in a pressure-sensitive adhesive layer, wherein a ketone group-containing pressure-sensitive adhesive is substantially crosslinked with a polyamine crosslinking agent. (See, for example, Patent document 3). However, no description is found of a tape preparation for percutaneous absorption having a pressure-sensitive adhesive comprising a copolymer with an acetoacetyl group.

There have also been known preparations for percutaneous absorption which contain an isosorbide dinitrate coronary vasodilator and a fatty acid ester in a crosslinked pressure-sensitive adhesive comprising an acrylic copolymer composed of an acrylic acid alkyl ester and a functional monomer as essential components. (See, for example, Patent document 4). However, this preparation for percutaneous absorption employs a crosslinking agent, and it is stated that without a crosslinking agent the pressure-sensitive adhesive layer lacks cohesive strength and cannot be used in a preparation for percutaneous absorption. In addition, Patent documents 3 and 4 do not provide examples of tape preparations for percutaneous absorption with pressure-sensitive adhesives comprising copolymers with acetoacetyl groups.

Patent document 1: Japanese Unexamined Patent Publication HEI No. 6-108033
Patent document 2: Japanese Unexamined Patent Publication HEI No. 7-238203
Patent document 3: Japanese Unexamined Patent Publication No. 2002-535475
Patent document 4: Japanese Unexamined Patent Publication HEI No. 8-81369

DISCLOSURE OF THE INVENTION

Problems to be Solved by the Invention

It is an object of the present invention to provide a medicinal tape preparation for percutaneous absorption having a drug-containing pressure-sensitive adhesive layer formed on a support and a release liner laminated thereover, wherein a large amount of a lipophilic oily substance can be included in the pressure-sensitive adhesive layer and the preparation has excellent adhesion, cohesive strength and stability, as well as a nonaqueous pressure-sensitive adhesive for the preparation.

The pressure-sensitive adhesive layer of the medicinal tape preparation for percutaneous absorption may also contain, in addition to a drug, also a solvent for dissolution of the drug, a percutaneous absorption accelerator to accelerate the percutaneous absorption rate of the drug, a plasticizer for improved plasticity of the pressure-sensitive adhesive or a tackifier for improved adhesive strength, and in some cases it may be necessary to include such components in significant amounts. The drug-dissolving solvent, percutaneous absorption accelerator, plasticizer and tackifier included with the drug in the pressure-sensitive adhesive layer will usually be lipophilic oily substances.

Problems have been encountered with conventional medicinal tape preparations for percutaneous absorption employing a non-crosslinked pressure-sensitive adhesive, in that it has not been possible to hold large amounts of oily substances, or when large amounts of oily substances are contained it has not been possible to form tape preparations and the oily substances have separated from the pressure-sensitive adhesive layers after formation of the preparations, and therefore the amounts of oily substances in pressure-sensitive adhesive layers have been limited.

In order to overcome these problems, there have also been studied tape preparations wherein a pressure-sensitive adhesive obtained by polymerizing a functional group-containing monomer is crosslinked with a crosslinking agent such as a polyamine compound, isocyanate compound or polyvalent metal chelate compound. However, such crosslinking agents are often toxic compounds or they have undesirable effects on certain drugs, while restrictions are necessary on their use or the amounts of their use.

Self-crosslinking pressure-sensitive adhesives employing no crosslinking agents are known, such as pressure-sensitive adhesives comprising N-methylolacrylamide as a constituent monomer, but such adhesives are not preferred for medicinal pressure-sensitive adhesive tapes due to gradually release of the harmful substance formaldehyde.

There are also known copolymers comprising acetoacetyl group-containing monomers as constituent monomers, for use as paints, coating agents and adhesives, but all such compounds are crosslinked using crosslinking agents such as polyamine derivatives, isocyanate compounds and polyvalent metal chelate compounds, and their use in medicinal tape preparations for percutaneous absorption is not known. In addition, these crosslinking agents are associated with such problems as toxicity and unsuitability for certain types of drugs.

Means for Solving the Problems

As a result of much research conducted with the aim of solving the problems described above, the present inventors discovered that it is possible to hold large amounts of oily substances such as plasticizers by using a nonaqueous pressure-sensitive adhesive comprising a copolymer obtained by copolymerization of a (meth)acrylic monomer having an acetoacetyl group in the molecule and one or more monomers selected from among other (meth)acrylic monomers with no acetoacetyl group and copolymerizable vinyl monomers, in a nonaqueous solvent.

The nonaqueous pressure-sensitive adhesive used in the medicinal tape preparation for percutaneous absorption of the invention, comprising a copolymer obtained by copolymerization of a (meth)acrylic monomer having an acetoacetyl group and one or more vinyl monomers selected from among other (meth)acrylic monomers with no acetoacetyl group and copolymerizable vinyl monomers, in a nonaqueous solvent, undergoes self-crosslinking of the acetoacetyl groups as the solvent evaporates during the step of coating onto a support or release film together with a drug and plasticizer followed by heating to dryness, thereby forming a network structure with the oily substances such as the plasticizer held in the network structure.

By adjusting the amount of acetoacetyl group-containing (meth)acrylic monomer in the starting material, it is possible to alter the degree of self-crosslinking of the pressure-sensitive adhesive. It was discovered that, as a result, it is possible to adjust the content of lipophilic oily substances such as plasticizers, percutaneous absorption accelerators, drug dissolving agents and the like in the pressure-sensitive adhesive layer, and that by modifying the content ratio of the pressure-sensitive adhesive and the plasticizer or percutaneous absorption accelerator it is possible to produce suitable adhesion and cohesive strength and obtain a stable tape preparation for percutaneous absorption; the present invention was completed on the basis of this discovery.

Effect of the Invention

In the step of heat drying the nonaqueous pressure-sensitive adhesive copolymer comprising a (meth)acrylic monomer having an acetoacetyl group as a constituent monomer according to the invention, a network structure is formed by self-crosslinking of the acetoacetyl groups as the solvent evaporates, so that large amounts of oily substances such as the plasticizer can be included in the network structure. The pressure-sensitive adhesive of the invention uses no polyamine derivatives, isocyanate compounds or polyvalent metal chelate compounds as crosslinking agents, and therefore since toxicity is not a concern and the skin is not irritated, the adhesive is suitable for medical use. The medicinal tape preparation for percutaneous absorption of the invention has excellent adhesive and cohesive strength, and is highly safe with low skin irritation. Its properties of drug release and percutaneous absorption are also excellent.

BEST MODE FOR CARRYING OUT THE INVENTION

The nonaqueous pressure-sensitive adhesive for a medicinal tape preparation for percutaneous absorption according to the invention may be obtained by copolymerization of a (meth)acrylic monomer having an acetoacetyl group in the same molecule and one or more monomers selected from among (meth)acrylic monomers with no acetoacetyl group and copolymerizable vinyl monomers, in a nonaqueous solvent.

As (meth)acrylic monomers having an acetoacetyl group there may be mentioned acetoacetoxyalkyl methacrylates or acetoacetoxyalkyl acrylates such as 2-acetoacetoxyethyl methacrylate, 2-acetoacetoxyethyl acrylate, 3-acetoacetoxypropyl methacrylate, 3-acetoacetoxypropyl acrylate, 4-acetoacetoxybutyl methacrylate and 4-acetoacetoxybutyl acrylate, among which any one or more may be used, although 2-acetoacetoxyethyl methacrylate and 2-acetoacetoxyethyl acrylate are preferred.

As other (meth)acrylic monomers having no acetoacetyl group there may be used any (meth)acrylic monomers having a copolymerizable double bond in the molecule, and one or more such (meth)acrylic monomers may be used. As specific examples there may be mentioned one or more (meth)acrylic monomers selected from the group consisting of 2-ethylhexyl acrylate, 2-ethylhexyl methacrylate, diacetoneacrylamide, butyl acrylate, butyl methacrylate, ethyleneglycol dimethacrylate, diethyleneglycol dimethacrylate, triethyleneglycol methacrylate, tetraethyleneglycol diacrylate, tetraethyleneglycol dimethacrylate, hexaethyleneglycol dimethacrylate, hexaethyleneglycol diacrylate, methyl methacrylate, acrylamide, methacrylamide, 2-hydroxyethyl acrylate and acrylic acid, of which there are preferred one or more acrylic monomers selected from the group consisting of 2-ethylhexyl acrylate, diacetoneacrylamide, butyl acrylate, tetraethyleneglycol diacrylate, tetraethyleneglycol dimethacrylate and methyl methacrylate.

The other vinyl compound which is copolymerizable with the monomer having an acetoacetyl group need only have a copolymerizable vinyl group in the molecule, and as examples there may be mentioned vinyl derivatives such as N-vinyl-2-pyrrolidone and vinyl acetate.

The content of the acetoacetyl group-containing monomer in the copolymer used in the nonaqueous pressure-sensitive adhesive of the invention is preferably 1-40 wt % and more preferably 5-40 wt % with respect to the total weight of the copolymer. The proportion is preferably not smaller than 1 wt %, because the oily substance-holding power and the cohesive strength will be reduced, and it is preferably not greater than 40 wt % because the network structure will become too dense, reducing the holding power for the plasticizer and other components.

The solvent of the nonaqueous pressure-sensitive adhesive for the medicinal tape preparation for percutaneous absorption according to the invention may be any organic solvent which volatilizes in the heat drying step during the production process for the medicinal tape preparation for percutaneous absorption of the invention. Such a solvent may be any of various organic solvents including acetic acid esters such as methyl acetate, ethyl acetate, propyl acetate and butyl acetate, aliphatic hydrocarbons such as hexane, heptane, octane and cyclohexane, aromatic hydrocarbons such as benzene, toluene and xylene, ketones such as acetone and methyl ethyl ketone, and ethers such as isopropyl ether, tetrahydrofuran and dioxane, among which any may be used alone, or two or more may be used in combination.

The nonaqueous pressure-sensitive adhesive of the invention may be produced by a well-known method in the relevant technical field. A specific preferred method is dissolution of each of the monomers in an organic solvent and polymerization with a radical initiator.

Alternatives include dissolution of all of the monomers in a prescribed organic solvent beforehand, nitrogen substitution, and then heating for polymerization, or successive loading of the monomer in separate amounts into the solvent for polymerization. The monomer concentration in the organic solvent is preferably 10-80 wt %. The concentration is preferably not less than 10 wt % because it will be difficult to achieve a high polymerization degree, while it is preferably not greater than 80 wt % because control of the heat of polymerization during the reaction will become difficult. The organic solvent used for the polymerization may be any single solvent selected from the group consisting of organic solvents mentioned above, or a combination of two or more thereof. Also, the same type or different types of solvents may be added successively during the polymerization.

The radical initiator used for the invention may be a compound selected from among peroxides, azo initiators and the like, or a mixture thereof, and it is used in an amount of preferably 0.001-2.00 parts by weight and more preferably 0.005-0.1 part by weight to 100 parts by weight of the monomer.

As specific peroxides there may be mentioned benzoyl peroxide, lauroyl peroxide, tert-butyl hydroperoxide, di(2-ethylhexyl)peroxydicarbonate and 1,1'-di-tert-butyl-peroxy-2-methylcyclohexane. As specific azo initiators there may be mentioned 2,2'-azobisisobutyronitrile, 4,4'-azobis-4-cyanovaleric acid and 2,2'-azobis(2-amidinopropane)dihydrochloride.

The polymerization temperature may be a temperature at which the radical initiator generates a suitable level of radicals, and in most cases it is preferably 50-120° C.

The amount of residual monomer of the nonaqueous pressure-sensitive adhesive of the invention is preferably minimized for reduced skin irritation and improved drug stability, and preferably it is no greater than 20,000 ppm with respect to the solid portion of the pressure-sensitive adhesive. In order to reduce the residual monomer, for example, additional radical initiator may be added after completion of the polymerization, or high-temperature treatment may be carried out under pressurized conditions.

A greater molecular weight of the copolymer of the pressure-sensitive adhesive of the invention will result in inferior adhesion, while a smaller molecular weight will result in inferior cohesive strength. The molecular weight of the copolymer may be a weight-average molecular weight of between several tens of thousands to several million.

The glass transition temperature (hereinafter also referred to as "Tg") of the copolymer of the pressure-sensitive adhesive of the invention also has a significant effect on the adhesive and cohesive strength of the pressure-sensitive adhesive, with a high Tg tending to result in a harder pressure-sensitive adhesive and a low Tg tending to results in a softer one, and therefore the Tg of the copolymer is preferably in the range of −60° C. to −5° C. The range is more preferably between −50° C. and −10° C. If it is below −60° C., the cohesive strength of the pressure-sensitive adhesive will tend to be too weak when the plasticizer is added, while a Tg of higher than −5° C. will tend to result in poor adhesive strength even with addition of a large amount of plasticizer.

The glass transition temperature can generally be determined by measurement with a DSC apparatus or measurement of the viscoelasticity. It can also be derived by calculation using the following formula 1, as the glass transition temperature of the homopolymer.

$$\frac{100}{Tg} = \sum \frac{Wi}{Tgi} \quad (1)$$

(wherein Wi represents the weight fraction (%) of the monomer of component {"i", and Tgi represents the glass transition temperature (° K) of the homopolymer of component "i".)

The plasticizer included in the pressure-sensitive adhesive layer of the medicinal tape preparation for percutaneous absorption of the invention may be an oily substance with a high boiling point in most cases. For example, there may be used fatty acid ester derivatives such as isopropyl myristate, diethyl sebacate, diisopropyl adipate, ethyl oleate, isopropyl palmitate, ethyl laurate, octyl palmitate, isotridecyl myristate and medium-chain fatty acid triglycerides; higher alcohol derivatives such as hexyldecanol and octyldodecanol; polyalkylene glycols such as polyethylene glycol and polypropylene glycol; and fats and oils such as olive oil, castor oil and the like. These may be used alone or in mixtures of two or more, but isopropyl myristate and isopropyl palmitate are most preferred because they function as plasticizers for the pressure-sensitive while also accelerating diffusion of the drug in the tape preparation and promoting skin permeability of the drug. The plasticizer content is preferably no greater than 50 wt % and more preferably 10-40 wt % with respect to the total weight of the pressure-sensitive adhesive layer. The plasticizer content is preferably not greater than 50 wt % because such an amount cannot be held in the pressure-sensitive adhesive layer, and the oily substances will tend to bleed from the pressure-sensitive adhesive layer.

The pressure-sensitive adhesive in the pressure-sensitive adhesive layer of the medicinal tape preparation for percutaneous absorption of the invention exhibits suitable adhesive strength even alone if it contains a percutaneous absorbing drug and a plasticizer in addition to the nonaqueous pressure-sensitive adhesive, but if even stronger adhesive strength is desired, a tackifier may be included in the pressure-sensitive adhesive layer to increase the adhesive strength, and examples of tackifiers that are suitable for use include alicyclic saturated hydrocarbon resins and rosin ester derivatives. Alicyclic saturated hydrocarbon resins include ALCON P-100 (trade name of Arakawa Chemical Industries Co., Ltd.) while rosin ester derivatives include ESTERGUM H (trade name of Arakawa Chemical Industries Co., Ltd.), and any one or mixtures of two or more may be used.

There are no particular restrictions on drugs to be formulated in the tape preparation for percutaneous absorption of the invention, and they may be selected to conform to the purpose of treatment; examples of suitable drugs include steroid hormones, non-steroidal anti-inflammatory drugs, tranquilizers, anti-hypertensive agents, ischemic heart disease drugs, anti-histamines, antiasthmatic drugs, anti-Parkinson drugs, cerebral circulation improvers, antiemetics, antidepressants, anti-dementia drugs, Sjogren's syndrome treatments, anti-arrhythmia drugs, anticoagulants, gout suppressants, antifungal agents, narcotic analgesics, beta blockers, β1 agonists, β2 agonists, antitumor agents, diuretics, antithrombotic agents, histamine H1 receptor antagonists, histamine H2 receptor antagonists, anti-allergic agents, serotonin receptor antagonists, anti-hypercholesteremic agents and smoking cessation aids, and any percutaneously absorbed drugs may be used which do not reside on the skin surface but penetrate to the subcutaneous layer or into the blood to exhibit a local or systemic effect. Two or more of such drugs may also be used together if necessary. Also, the contents of the drugs may be appropriately set depending on the type of drug, its effect and the purpose of administration.

If necessary, the pressure-sensitive adhesive layer of the tape preparation for percutaneous absorption of the invention may also include, in addition to the aforementioned drug, pressure-sensitive adhesive and plasticizer, also a drug solubilizer, percutaneous absorption accelerator and other excipients.

A drug solubilizer is a drug-dissolving solvent, and any solvent which is not skin-irritating may be used. Specifically, there may be used lower alcohols such as ethanol, propanol and isopropanol, medium alcohols such as hexanol and octanol, polyhydric alcohols such as glycerin, ethylene glycol and diethyleneglycol, fatty acid esters, polyvinyl alcohols, N-methylpyrrolidone, crotamiton and the like, any of which may be used alone or in combinations of two or more as drug-dissolving agents, although there is no limitation to these.

As drug percutaneous absorption accelerators there may be used any which are commonly utilized in tape preparations for percutaneous absorption, including fatty acid esters such as isopropyl myristate, isopropyl palmitate and diisopropyl adipate, fatty acid polyhydric alcohol esters such as caprylic monoglyceride, caprylic triglyceride and sorbitan fatty acid esters, and terpenes such as 1-menthol, peppermint oil and limonene.

Examples of excipients include silicon compounds such as silicic anhydride and light silicic anhydride, cellulose derivatives such as ethyl cellulose, methyl cellulose, carboxymethylcellulose sodium, hydroxypropyl cellulose and hydroxypropylmethyl cellulose, water-soluble polymers such as polyvinyl alcohol, antioxidants such as dibutylhydroxytoluene and powders such as kaolin and titanium oxide, as well as aromatics and coloring agents, and these may be added in medically acceptable ranges.

There are no particular restrictions on the support for the tape preparation for percutaneous absorption of the invention, and there may be used stretchable or non-stretchable woven or nonwoven fabric or knit textiles made of polyethylene, polypropylene, polyester or the like, plastic films made of polyethylene, polypropylene, polyester, ethylene-vinyl acetate copolymer, vinyl chloride or the like, or foam films made of polyurethane or the like, either alone or in laminated combinations, depending on the purpose of use.

The release liner on the tape preparation for percutaneous absorption of the invention serves to protect the pressure-sensitive adhesive layer during storage, and there may be used polyester, polyethylene, polypropylene, ethylene-vinyl acetate copolymer resin, polyurethane, a metal foil thin-film, a film having a laminated structure comprising a combination of such materials, a film which has been silicon-treated on the surface to be attached to the pressure-sensitive adhesive layer, or a film having a metal such as aluminum vapor-deposited on the surface. In addition, the release liner may be provided with a continuous or non-continuous straight or curved notch for easier release.

The tape preparation for percutaneous absorption of the invention may be produced by coating the surface of the release liner with a solution containing the drug, plasticizer and if necessary a drug-dissolving agent or percutaneous absorption accelerator, with the pressure-sensitive adhesive, and then heating to dryness at a temperature of 40-150° C. to form a pressure-sensitive adhesive layer, subsequently laminating a support on the surface of the pressure-sensitive adhesive layer opposite the side on which the release liner is attached, and cutting it to an appropriate size. When a non-water-permeable support is used as the support, a pressure-sensitive adhesive solution containing the drug, plasticizer, etc. may be applied onto the support and heated to dryness, and then the release liner laminated thereon. The temperature for heating to dryness may be a temperature above the volatilization temperature of the solvent. The temperature is preferably not too low because the solvent will not completely volatilize, and it is preferably not above 150° C. because an adverse effect may be produced on the drug, plasticizer and percutaneous absorption accelerator.

EXAMPLES

The nonaqueous pressure-sensitive adhesive for the medicinal tape preparation for percutaneous absorption of the invention and the medicinal tape preparation for percutaneous absorption will now be further explained through the following examples, with the understanding that the invention is in no way limited to these examples.

Example 1

Production of Nonaqueous Pressure-Sensitive Adhesive 1

After charging 157.5 g of 2-ethylhexyl acrylate (hereinafter abbreviated as 2EHA), 35 g of 2-acetoacetoxyethyl methacrylate (hereinafter abbreviated as AAEM), 80.5 g of diacetoneacrylamide (hereinafter abbreviated as DAAM) and 76 g of methyl methacrylate (hereinafter abbreviated as MMA) in a 2-liter four-necked flask equipped with a Dimroth condenser, thermometer, nitrogen gas blow-in tube and stirrer, 525 g of ethyl acetate was added as a solvent and the mixture was dissolved to uniformity. The temperature was raised to 75° C. while blowing in nitrogen gas at flow rate of 100 ml/min. After holding at 75° C. for 30 minutes, a solution of 0.21 g of benzoyl peroxide as an initiator in 5 g of ethyl acetate was added, and the external temperature was set to 85° C. Subsequently, 300 g of toluene was loaded in portions of 100 g at a time at 3, 5 and 7 hours after adding the initiator. During the polymerization, nitrogen gas was continuously blown in at a flow rate of 100 ml/min.

At 12 hours after the final toluene loading, 0.35 g of benzoyl peroxide was loaded as an additional catalyst, and then heat treatment for 12 hours at an external temperature of 95° C. was followed by cooling to obtain nonaqueous pressure-sensitive 1.

Physical Properties of Solution of Nonaqueous Pressure-Sensitive Adhesive 1

Solution viscosity (measured with Brookfield viscometer): 30,000 mPa·s

Solid portion (150° C.×1 hour treatment): 28.5%

Residual monomers: 300 ppm 2EHA, 20 ppm AAEM, 1000 ppm DAAM, 150 ppm MMA (measured by HPLC).

Example 2

Production of Nonaqueous Pressure-Sensitive Adhesive 2

A monomer solution was prepared by uniformly pre-dissolving 78.8 g of 2EHA, 78.8 g of n-butyl acrylate (hereinafter abbreviated as BA), 105 g of AAEM, 87.5 g of MMA and 1.05 g of diethyleneglycol dimethacrylate (hereinafter abbreviated as DEGMA). After adding 100 g of the monomer solution in a 2-liter four-necked flask equipped with a Dimroth condenser, thermometer, nitrogen gas blow-in tube and stirrer, 350 g of ethyl acetate was added as a solvent. The temperature was raised to 75° C. while blowing in nitrogen gas at flow rate of 100 ml/min, and after holding at 75° C. for 30 minutes, a solution of 0.35 g of benzoyl peroxide as an initiator in 5 g of ethyl acetate was added, and the external temperature was set to 85° C. Upon confirming reflux of the solvent, the remaining monomer solution was loaded continuously for 3 hours. Next, one hour after the initial continuous loading of the monomer solution, 500 g of ethyl acetate was continuously loaded for 3 hours. After continuing to stir for 12 hours after loading the ethyl acetate, 0.5 g of benzoyl peroxide was loaded as additional catalyst and then heat treatment for 12 hours was followed by cooling to obtain nonaqueous pressure-sensitive 2. During the polymerization, nitrogen gas was continuously blown in at a flow rate of 100 ml/min.

Physical Properties of Solution of Nonaqueous Pressure-Sensitive Adhesive 2

Solution viscosity (measured with Brookfield viscometer): 25,000 mPa·s

Solid portion (150° C.×1 hour treatment): 27.5%

Residual monomers: 1000 ppm 2EHA, 200 ppm BA, 100 ppm AAEM, 250 ppm MMA, DEGMA below detection limit (measured by HPLC).

Nonaqueous pressure-sensitive adhesives 3-10 for Examples 3-10 shown in Table 1 were produced by the method described in Example 2.

Comparative Example 1

Production of Comparison Pressure-Sensitive Adhesive 1

Polymerization and synthesis were conducted by the same method as for pressure-sensitive adhesive 1 of Example 1 using a monomer composition of 90 g 2EHA, 90 g BA, 80.5 g DAAM, 87.5 g MMA and 1.0 g DEGMA, to produce comparison pressure-sensitive adhesive 1.

Physical Properties of Solution of Comparison Pressure-Sensitive Adhesive 1

Solution viscosity (measured with Brookfield viscometer): 38,000 mPa·s

Solid portion (150° C.×1 hour treatment): 28.5%

Residual monomers: 300 ppm 2EHA, 200 ppm BA, 1500 ppm DAAM, 100 ppm MMA, DEGMA below detection limit (measured by HPLC).

Comparative Example 2

Preparation of Comparison Pressure-Sensitive Adhesive 2

Polymerization and synthesis were conducted by the same method as in Example 2 using a monomer composition of 130 g 2EHA, 130 g BA and 90 g MMA, to produce comparison pressure-sensitive adhesive 2.

Physical Properties of Solution of Comparison Pressure-Sensitive Adhesive 2

Solution viscosity (measured with Brookfield viscometer): 28,000 mPa·s

Solid portion (150° C.×1 hour treatment): 27.5%

Residual monomers: 500 ppm 2EHA, 300 ppm BA, 150 ppm MMA (measured by HPLC).

The monomer compositions, solvents and calculated Tg values for the nonaqueous pressure-sensitive adhesives of Examples 1-10 and Comparative Examples 1 and 2 are shown in Table 1.

TABLE 1

| | Nonaqueous pressure-sensitive adhesives | | | | | | | | |
|---|---|---|---|---|---|---|---|---|---|
| | Monomer | | | | | | | | Calculated Tg |
| Example | AAEM | DAAM | MMA | 2EHA | BA | DEGMA | TEGMA | Solvent | value |
| 1 | 10.0 | 23.1 | 21.8 | 45.1 | | | | EtOAc, toluene | −12.3 |
| 2 | 29.9 | | 24.9 | 22.5 | 22.5 | 0.2 | | EtOAc, toluene | −15.0 |
| 3 | 0.1 | | 28.9 | 35.4 | 35.4 | 0.2 | | EtOAc, toluene | −32.2 |
| 4 | 1.0 | | 29.0 | 34.8 | 35.0 | 0.2 | | EtOAc, toluene | −31.6 |
| 5 | 5.0 | | 25.0 | 34.8 | 35.0 | 0.2 | | EtOAc, toluene | −33.7 |
| 6 | 10.0 | | 10.0 | 40.0 | 39.8 | 0.2 | | EtOAc, toluene | −47.6 |
| 7 | 10.0 | 22.9 | 21.8 | 45.0 | | | 0.3 | EtOAc, toluene | −12.0 |
| 8 | 20.0 | | 20.0 | 29.8 | 30.0 | 0.2 | | EtOAc, toluene | −29.3 |
| 9 | 30.0 | | 25.0 | 22.4 | 22.4 | 0.2 | | EtOAc, toluene | −15.0 |
| 10 | 40.0 | | 19.9 | 20.0 | 19.9 | 0.2 | | EtOAc, toluene | −27.5 |

TABLE 1-continued

Nonaqueous pressure-sensitive adhesives

| Example | Monomer | | | | | | | Solvent | Calculated Tg value |
|---|---|---|---|---|---|---|---|---|---|
| | AAEM | DAAM | MMA | 2EHA | BA | DEGMA | TEGMA | | |
| Comp. Ex. 1 | 0 | 23.1 | 25.1 | 25.8 | 25.8 | 0.2 | | EtOAc, toluene | −9.2 |
| Comp. Ex. 2 | 0 | | 25.8 | 37.1 | 37.1 | | | EtOAc, toluene | −36 |

AAEM: 2-acetoacetoxyethyl methacrylate; DAAM: diacetoneacrylamide; MMA: methyl methacrylate; 2EHA: 2-ethylhexyl acrylate; BA: n-butyl acrylate; DEGMA: diethyleneglycol dimethacrylate; TEGMA: tetraethyleneglycol dimethacrylate; EtOAc: ethyl acetate
The values in the monomer columns are the weight percentages of each monomer with respect to 100 as the total dry copolymer weight.

Test Example 1

The nonaqueous pressure-sensitive adhesives 1-10 of the invention and the comparison pressure-sensitive adhesives 1 and 2 shown in Table 1, and the commercially available acrylic solvent-type (nonaqueous) pressure-sensitive adhesive S-3403 (ARONTACK S-3403, trade name of Toa Gosei Co., Ltd.) were used for coating and drying onto a support to produce tapes 2-1 to 2-21 and comparison tapes 3-5, and the compatibility of the pressure-sensitive adhesives and oily substances, the adhesive and cohesive strengths of the pressure-sensitive adhesives were evaluated.

1) Tape Production Methods
Production of Tape 2-1

A 38.69 g portion of pressure-sensitive adhesive 1 was placed in a screw-cap bottle and stirred for more than an hour in the bottle. A coating tester (LTE-S, Wener Mathis AG) was used for coating and drying of the solution onto a support (polyester film) to a dried coating weight of 70 mg/10 cm$^2$, and then a liner (silicon-treated polyester film) was used to cover it with the silicon side contacting the pressure-sensitive to obtain tape 2-1.

Production of Tape 2-2

A 38.69 g portion of pressure-sensitive adhesive 1, and then 1.2 g of isopropyl myristate (IPM), were placed in a screw-cap bottle and stirred for more than an hour in the bottle. A coating tester (LTE-S, Wener Mathis AG) was used for coating and drying of the solution onto a support (polyester film) to a dried coating weight of 70 mg/10 cm$^2$, and then a liner (silicon-treated polyester film) was used to cover it with the silicon side contacting the pressure-sensitive to obtain tape 2-2.

Pressure-sensitive adhesives and corresponding plasticizers were used in the same method as the production method of tape 2-2 to produce tapes 2-3 to 2-21 and comparison tape 3-5.

2) Evaluation of Compatibility between Pressure-Sensitive Adhesives and Oily Substances The preparation liners were released and an optical microscope was used to observe the condition of liquid substance adhering to the liner surface.

Evaluation:
○: No liquid substance on the liner surface
x: Liquid substance on the liner surface 3) Evaluation of Tape Adhesive Strength After releasing the liner of the preparation, the pressure-sensitive adhesive side was touched with a finger and evaluated based on the following evaluation scale.

○: (excellent) Adhesive strength comparable to MOHRUS TAPE (trade name of Hisamitsu Pharmaceutical) and YAKUBAN (trade name of Mikasa Seiyaku) which employ styrene-isoprene-styrene copolymer.

Δ: (good) Adhesive strength comparable to SERASTAR (trade name of Yamanouchi Pharmaceutical) and FALZY (trade name of Sawai Pharmaceutical) which employ natural rubber latex.

x: (poor) Adhesive strength below that of commercial products.

−: Evaluation impossible due to significantly low cohesive strength (semi-solid state).

4) Evaluation of Tape Cohesive Strength (Hardness)

After releasing the liner of the tape, the pressure-sensitive adhesive side was touched with a finger and evaluated based on the following evaluation scale.

Evaluation:
○: (excellent) Cohesive strength comparable to SERASTAR (trade name of Yamanouchi Pharmaceutical) and FALZY (trade name of Sawai Pharmaceutical) which employ natural rubber latex.

Δ: (good) Cohesive strength comparable to MOHRUS TAPE (trade name of Hisamitsu Pharmaceutical) and YAKUBAN (trade name of Mikasa Seiyaku) which employ styrene-isoprene-styrene copolymer.

x: (poor) Cohesive strength below that of commercial products.

Tapes 2-1 to 2-21 and comparison tape 3-5 were used for evaluation of the compatibility of the pressure-sensitive adhesives and oily substances, the adhesive and cohesive strengths, giving the results shown in Table 2. The comparison tapes 3 and 4, and comparison tape 5 which employed a commercially available acrylic pressure-sensitive adhesive, all exhibited inadequate adhesive and cohesive strength, while tapes 2-1 to 2-21 which were prepared using nonaqueous pressure-sensitive adhesives of the invention exhibited adequate adhesive and cohesive strength.

TABLE 2

Compatibilities, adhesive strengths and cohesive strengths of nonaqueous pressure-sensitive adhesive tapes

| Tape No. | Monomer | | | | | | | Solvent | Plasticizer | Compatibility | Adhesive strength | Cohesive strength |
|---|---|---|---|---|---|---|---|---|---|---|---|---|
| | AAEM | DAAM | MMA | 2EHA | BA | DEGMA | TEGMA | | | | | |
| 2-1 | 10.0 | 23.1 | 21.8 | 45.1 | | | | EtOAc, toluene | — | ○ | ○ | ○ |
| 2-2 | 10.0 | 23.1 | 21.8 | 45.1 | | | | EtOAc, toluene | IPM 10 | ○ | ○ | ○ |

TABLE 2-continued

Compatibilities, adhesive strengths and cohesive strengths of nonaqueous pressure-sensitive adhesive tapes

| Tape No. | AAEM | DAAM | MMA | 2EHA | BA | DEGMA | TEGMA | Solvent | Plasticizer | Compatibility | Adhesive strength | Cohesive strength |
|---|---|---|---|---|---|---|---|---|---|---|---|---|
| 2-3 | 10.0 | 23.1 | 21.8 | 45.1 | | | | EtOAc, toluene | IPM 20 | ○ | ○ | ○ |
| 2-4 | 10.0 | 23.1 | 21.8 | 45.1 | | | | EtOAc, toluene | IPM 30 | ○ | ○ | ○ |
| 2-5 | 10.0 | 23.1 | 21.8 | 45.1 | | | | EtOAc, toluene | IPM 40 | ○ | ○ | ○ |
| 2-6 | 10.0 | 23.1 | 21.8 | 45.1 | | | | EtOAc, toluene | IPP 20 | ○ | ○ | ○ |
| 2-7 | 10.0 | 23.1 | 21.8 | 45.1 | | | | EtOAc, toluene | HD 20 | ○ | ○ | ○ |
| 2-8 | 10.0 | 23.1 | 21.8 | 45.1 | | | | EtOAc, toluene | DES 20 | ○ | ○ | ○ |
| 2-9 | 10.0 | 23.1 | 21.8 | 45.1 | | | | EtOAc, toluene | DPA 20 | ○ | ○ | ○ |
| 2-10 | 10.0 | 23.1 | 21.8 | 45.1 | | | | EtOAc, toluene | MFTG 20 | ○ | ○ | ○ |
| 2-11 | 10.0 | 23.1 | 21.8 | 45.1 | | | | EtOAc, toluene | PETA 20 | ○ | ○ | ○ |
| 2-12 | 10.0 | 23.1 | 21.8 | 45.1 | | | | EtOAc, toluene | Castor oil 20 | ○ | ○ | ○ |
| 2-13 | 29.9 | | 24.9 | 22.5 | 22.5 | 0.2 | | EtOAc, toluene | IPM 20 | ○ | ○ | ○ |
| 2-14 | 0.1 | | 28.9 | 35.4 | 35.4 | 0.2 | | EtOAc, toluene | IPM 20 | ○ | ○ | Δ |
| 2-15 | 1.0 | | 29.0 | 34.8 | 35.0 | 0.2 | | EtOAc, toluene | IPM 20 | ○ | ○ | ○ |
| 2-16 | 5.0 | | 25.0 | 34.8 | 35.0 | 0.2 | | EtOAc, toluene | IPM 20 | ○ | ○ | ○ |
| 2-17 | 10.0 | | 10.0 | 40.0 | 39.8 | 0.2 | | EtOAc, toluene | IPM 20 | ○ | ○ | ○ |
| 2-18 | 10.0 | 22.9 | 21.8 | 45.0 | | | 0.3 | EtOAc, toluene | IPM 20 | ○ | ○ | ○ |
| 2-19 | 20.0 | | 20.0 | 29.8 | 30.0 | 0.2 | | EtOAc, toluene | IPM 20 | ○ | ○ | ○ |
| 2-20 | 30.0 | | 25.0 | 22.4 | 22.4 | 0.2 | | EtOAc, toluene | IPM 20 | ○ | ○ | ○ |
| 2-21 | 40.0 | | 19.9 | 20.0 | 19.9 | 0.2 | | EtOAc, toluene | IPM 20 | ○ | ○ | ○ |
| Comp. Ex. 3 | 0 | 23.1 | 25.1 | 25.8 | 25.8 | 0.2 | | EtOAc, toluene | IPM 20 | ○ | — | x |
| Comp. Ex. 4 | 0 | | 25.8 | 37.1 | 37.1 | | | EtOAc, toluene | IPM 20 | ○ | — | x |
| Comp. Ex. 5 | Acrylic solvent-type pressure-sensitive adhesive: S-3403 (ARONTACK S-3403 Toa Gosei Co., Ltd.) | | | | | | | | IPM 20 | ○ | — | x |

AAEM: 2-acetoacetoxyethyl methacrylate; DAAM: diacetoneacrylamide; MMA: methyl methacrylate; 2EHA: 2-ethylhexyl acrylate; BA: n-butyl acrylate; DEGMA: diethyleneglycol dimethacrylate; TEGMA: tetraethyleneglycol dimethacrylate; EtOAc: ethyl acetate; IPM: isopropyl myristate; IPP: isopropyl palmitate; HD: hexyldecanol; DES: diethyl sebacate; DPA: diisopropyl adipate; MFTG: medium chain fatty acid triglyceride; PETA: polyester adipate.
The values in the monomer columns are the weight percentages of each monomer with respect to 100 as the total dry copolymer weight. The values in the plasticizer column are the weight percentages of each plasticizer with respect to 100 as the total weight of the pressure-sensitive adhesive layer.

Example 11

Production of Tape Preparation for Percutaneous Absorption 11

A 36.2 g portion of pressure-sensitive adhesive 7, and then 1.5 g of ketoprofen, were placed in a screw-cap bottle and stirred for more than an hour in the bottle. A coating tester (LTE-S, Wener Mathis AG) was used for coating and drying of the solution onto a support (polyester film) to a dried coating weight of 140 mg/10 cm$^2$, and then a liner (silicon-treated polyester film) was used to cover it with the silicon side contacting the pressure-sensitive to obtain tape preparation for percutaneous absorption 11. The ketoprofen content of the obtained preparation was 10 w/w %.

Example 12

Production of Tape Preparation for Percutaneous Absorption 12

A 35.69 g portion of pressure-sensitive adhesive 7, and then 3.0 g of IPM and 1.5 g of ketoprofen, were placed in a screw-cap bottle and stirred for more than an hour in the bottle. A coating tester (LTE-S, Wener Mathis AG) was used for coating and drying of the solution onto a support (polyester film) to a dried coating weight of 140 mg/10 cm$^2$, and then a liner (silicon-treated polyester film) was used to cover it with the silicon side contacting the pressure-sensitive to obtain tape preparation for percutaneous absorption 12. The ketoprofen content of the obtained preparation was 10 w/w %.

Examples 13-16

Production of Tape Preparations for Percutaneous Absorption 13-16

Tape preparations for percutaneous absorption 13-16 were each produced by the same method as Example 11 or Example 12, using pressure-sensitive adhesive 7, a drug and if necessary IPM plasticizer.

Comparative Examples 6-9

Production of Comparison Tape Preparations for Percutaneous Absorption 6-9

Comparison tape preparations for percutaneous absorption 6-9 were produced by the same method as in Example 12, using a specific drug and plasticizer, with a commercially available solvent-type acrylic pressure-sensitive adhesive for Comparative Examples 8 and 9 and addition of an isocyanate crosslinking agent for Comparative Examples 6 and 7.

The compatibility evaluation and tape adhesive and cohesive strength evaluation described in Test Example 1 were conducted using the tape preparations for percutaneous absorption 11-16 obtained in Examples 11-16, and the comparison tape preparations for percutaneous absorption 6-9. The tape preparations for percutaneous absorption according to the invention exhibited satisfactory adhesive and cohesive strength, while the comparison tape preparations for percutaneous absorption exhibited inferior adhesive and cohesive strength. The results are shown in Table 3.

TABLE 3

Compatibilities, adhesive strengths and cohesive strengths of medicinal tapes for percutaneous absorption

| Example | Pressure-sensitive adhesive | Crosslinking agent (amount) | Plasticizer (amount) | Drug (amount) | Compatibility | Adhesive strength | Cohesive strength |
|---|---|---|---|---|---|---|---|
| 11 | Adhesive 7 | — | — | ketoprofen 10 | ○ | ○ | ○ |
| 12 | Adhesive 7 | — | IPM 20 | ketoprofen 10 | ○ | ○ | ○ |
| 13 | Adhesive 7 | — | — | indomethacin 10 | ○ | ○ | ○ |
| 14 | Adhesive 7 | — | IPM 20 | indomethacin 10 | ○ | ○ | ○ |
| 15 | Adhesive 7 | — | — | tulobuterol 10 | ○ | ○ | ○ |
| 16 | Adhesive 7 | — | IPM 20 | tulobuterol 10 | ○ | ○ | ○ |
| Comp. Ex. 6 | Nissetsu PE300 | CK101 0.1 | IPM 20 | ketoprofen 10 | ○ | — | x |
| Comp. Ex. 7 | Nissetsu PE300 | CK101 0.1 | IPM 20 | indomethacin 10 | ○ | — | x |
| Comp. Ex. 8 | Nissetsu PE300 | | | tulobuterol 10 | ○ | — | x |
| Comp. Ex. 9 | Nissetsu PE300 | | IPM 20 | tulobuterol 10 | ○ | — | x |

CK101: isocyanate crosslinking agent CK101 (Nippon Carbide Industries Co., Ltd.).
Nissetsu PE300: Solvent-type acrylic pressure-sensitive adhesive, Nissetsu PE300 (Nippon Carbide Industries Co., Ltd.); IPM: isopropyl myristate.
The values for the crosslinking agents, plasticizers and drugs are weight percentages with respect to 100 as the total dry weight of the pressure-sensitive adhesive layer.

Test Example 2

Drug Release Test

Each preparation was applied onto extracted skin of a Yucatan micropig (YMP) and allowed to stand under conditions of 32° C.-60% RH. After 24 hours, the preparation was peeled off and the residual drug content of the preparation was measured by HPLC. The residual drug content was used to calculate the drug release rate (%) from the preparation.

(drug content before application−residual drug content)/drug content before application×100=drug release rate (%).

Test Example 3

Hairless Mouse Extracted Skin Permeability Test

After placing 0.05 mol/L McIlvaine Buffer (pH 7.4) on the cutis side (receiver side) of the extracted skin in a vertical diffusion cell, the preparation was applied to the horny layer side. The receiver solution was sampled at different time points, and then an equivalent amount of 0.05 mol/L McIlvaine Buffer was added. The drug concentration of the sampling solution was measured by HPLC, and the flux, lag time and 24 hr cumulative permeation were calculated.

A drug release test and skin permeability test were conducted for Test Examples 2 and 3, using the tape preparations for percutaneous absorption 15 and 16 of the examples and the tape preparations for percutaneous absorption 8 and 9 of the comparative examples. The results are shown in Table 4. The tape preparations for percutaneous absorption of the examples according to the invention had significantly superior drug release rates and skin permeabilities compared to the tape preparations for percutaneous absorption of the comparative examples.

Test Example 4

Cumulative Skin Irritation Test (Rabbit)

Rabbits used for the test were shaved on the back with an electric razor up to the day prior to the test.

The preparation was applied onto the back of a rabbit or guinea pig, impermeable oiled paper was laid thereover, a nonwoven fabric pressure-sensitive adhesive bandage (MESHPORE, Nichiban) was attached firmly over it, and the entire application site was covered with gauze and then covered with a pressure-sensitive adhesive elastic bandage (ELASTOPORE, Nichiban). After 6 hours, the test preparation was removed and the site of application was lightly scraped with absorbent cotton wetted with lukewarm water

TABLE 4

Drug release rates and skin permeabilities of medicinal tapes for percutaneous absorption

| | Pressure-sensitive adhesive | Plasticizer (amount) | Drug (concentration) | Release rate (%) | Lag Time (hr) | FLUX ($\mu g/cm^2/hr$) | Cumulative permeation ($\mu g/cm^2/24$ hr) |
|---|---|---|---|---|---|---|---|
| Example 15 | Adhesive 7 | — | tulobuterol 10 | 95.7 ± 0.8 | 2.31 ± 0.98 | 1.757 ± 0.398 | 17.71 ± 4.27 |
| Example 16 | Adhesive 7 | IPM 20 | tulobuterol 10 | 96.1 ± 0.3 | 0.17 ± 0.17 | 3.620 ± 0.057 | 29.40 ± 1.23 |
| Comp. Ex. 8 | Nissetsu PE-300 | — | tulobuterol 10 | 88.9 ± 0.2 | 5.14 ± 1.93 | 0.335 ± 0.133 | 3.30 ± 1.12 |
| Comp. Ex. 9 | Nissetsu PE-300 | IPM 20 | tulobuterol 10 | 83.0 ± 0.4 | 1.10 ± 0.28 | 2.238 ± 0.008 | 20.98 ± 2.24 |

IPM: isopropyl myristate; Nissetsu PE300: Solvent-type acrylic pressure-sensitive adhesive Nissetsu PE300 (Nippon Carbide Industries Co., Ltd.).
The values for the plasticizer and drug are the weight percentages with respect to 100 as the total weight of the pressure-sensitive adhesive layer.

and allowed to stand for 30 minutes, after which the site of application was observed. After observation was complete, the test preparation was applied at the same site and the same procedure was repeated for 7 days. The application site was observed in the same manner at 48 and 72 hours after final removal of the preparation, and a rating was assigned based on the following evaluation scale of Draize et al.

Evaluation scale of Draize et al.

A: Erythema and Scab Formation

No erythema: 0; Very mild erythema: 1; Apparent erythema: 2; Medium to severe erythema: 3; Severe erythema to slight scab formation: 4.

B: Edema Formation

No edema: 0; Very mild edema: 1; Mild edema: 2; Moderate edema (approximately 1 mM protrusions): 3; Severe edema: 4.

The 7-day cumulative skin irritation test described in Test Example 4 was conducted using a Japanese Pharmacopeia bandage and tapes 2-18 of the invention shown in Table 2, and the rabbit skin cumulative skin irritation scores were determined. As a result, the score for tapes 2-18 using pressure-sensitive adhesives of the invention was 4.0 while the score for the Japanese Pharmacopeia bandage was 14.6, thus indicating that the pressure-sensitive adhesives of the invention are highly safe, with low irritation on rabbit skin.

TABLE 5

Rabbit 7-day cumulative skin irritation test

|  | Cumulative irritation (7 days) |
|---|---|
| Japan Pharmacopeia bandage | 14.6 |
| Invention tapes 2-18 | 4.0 |

The average scores were calculated by the following formula. The 7-day cumulative irritation represents the cumulative total of the average scores from day 1 to day 9.

Average score=[(total of erythema scores)+(total of edema scores)]/5.

INDUSTRIAL APPLICABILITY

In the process of heat drying, the nonaqueous pressure-sensitive adhesive of the invention forms a network structure by self-crosslinking of the acetoacetyl groups, so that large amounts of oily substances such as the plasticizer can be included in the network structure. The pressure-sensitive adhesive of the invention uses no polyamine derivatives, isocyanate compounds, polyvalent metal chelate compounds or the like as crosslinking agents, and therefore since toxicity is not a concern and the skin is not irritated, the adhesive is suitable for medical use. The medicinal tape preparation for percutaneous absorption of the invention is superior from the standpoint of adhesive strength, cohesive strength, safety, drug release property and percutaneous absorption.

What is claimed is:

1. A non-aqueous pressure-sensitive adhesive for use in a medicinal tape preparation for percutaneous absorption, wherein the adhesive comprises a copolymer obtainable by copolymerization of (i) 2-acetoacetoxyethyl methacrylate and (ii) diacetoneacrylamide, 2-ethylhexyl acrylate, methyl methacrylate and tetraethyleneglycol dimethacrylate in a non-aqueous solvent, and wherein the copolymer consists of the five recited components.

2. The adhesive of claim 1, wherein the copolymer has a calculated glass transition temperature (Tg) of between −60° C. and −5° C.

3. A medicinal tape preparation for percutaneous absorption comprising
   (a) a support,
   (b) a pressure-sensitive adhesive layer containing a drug and a non-aqueous pressure-sensitive adhesive of claim 1, wherein the drug is a percutaneously absorbing drug selected from the group consisting of steroid hormones, non-steroidal anti-inflammatory drugs, tranquilizers, anti-hypertensive agents, anti-histamines, anti-asthmatic drugs, anti-Parkinson drugs, cerebral circulation improvers, anti-emetics, anti-depressants, anti-dementia drugs, Sjogren's syndrome treatments, anti-arrhythmia drugs, anti-coagulants, gout suppressants, anti-fungal agents, narcotic analgesics, beta blockers, β1 agonists, β2 agonists, anti-tumor agents, diuretics, anti-thrombotic agents, histamine H1 receptor antagonists, histamine H2 receptor antagonists, anti-allergic agents, serotonin receptor antagonists, anti-hypercholesteremic agents and smoking cessation aids, and
   (c) a release film, laminated together in that order.

4. The medicinal tape preparation of claim 3, wherein the pressure-sensitive adhesive layer further comprises a plasticizer.

5. The medicinal tape preparation of claim 4, wherein the plasticizer is one or more oils selected from the group consisting of fatty acid esters, higher alcohols and castor oil.

6. The medicinal tape preparation of claim 4, wherein the plasticizer content is no greater than 50 wt % of the total weight of said pressure-sensitive adhesive layer.

7. The medicinal tape preparation of claim 4, wherein the plasticizer is one or more fatty acid esters selected from the group consisting of isopropyl myristate, isopropyl palmitate, medium-chain fatty acid triglycerides, diethyl sebacate and diisopropyl adipate.

8. The medicinal tape preparation of claim 7, wherein the plasticizer is isopropyl myristate.

9. A process for production of a medicinal tape preparation of claim 3, comprising
   (a) selecting the release film or the support and coating a surface thereof with the non-aqueous pressure-sensitive adhesive, wherein the adhesive comprises the drug and optionally a plasticizer,
   (b) heating the coated surface to dryness to form a pressure-sensitive adhesive layer on the selected component of (a), and
   (c) laminating the unselected component of (a) thereon.

10. The process of claim 9, wherein the heating is at a temperature of from 40° C. to 150° C.

* * * * *